United States Patent
Rao

(10) Patent No.: US 8,168,172 B2
(45) Date of Patent: *May 1, 2012

(54) **PROCESS FOR THE PRODUCTION OF ORGANIC FORMULATION OF BIO-PESTICIDE *PSEUDOMONAS FLUORESCENS***

(75) Inventor: Mahendrakar Sreenivasa Rao, Bangalore (IN)

(73) Assignees: Department of Biotechnology, New Delhi (IN); Indian Institute of Horticultural Research, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 12/300,222

(22) PCT Filed: Sep. 10, 2007

(86) PCT No.: PCT/IN2007/000401
§ 371 (c)(1),
(2), (4) Date: Aug. 12, 2009

(87) PCT Pub. No.: WO2008/139488
PCT Pub. Date: Nov. 20, 2008

(65) Prior Publication Data
US 2010/0167380 A1    Jul. 1, 2010

(30) Foreign Application Priority Data
May 10, 2007  (IN) .................. 1019/DEL/07

(51) Int. Cl.
*A01N 63/00* (2006.01)
*C12N 1/20* (2006.01)

(52) U.S. Cl. .................. 424/93.47; 435/253.3; 435/876; 504/117

(58) Field of Classification Search .................. None
See application file for complete search history.

(56) References Cited

FOREIGN PATENT DOCUMENTS

| IN | 1404DEL2004 A | | 7/2006 |
|---|---|---|---|
| IN | 200401404 | * | 7/2006 |

OTHER PUBLICATIONS

Khan et al. Phytopathologia Mediterranea, Aug. 2005, vol. 44, No. 2, pp. 208-215.*
Padmodaya et al. Journal of Mycology and Plant Pathology, Apr. 1999, vol. 29, No. 1, pp. 38-41.*
Saravanan et al. Crop Protection, 2003, 22, pp. 1117-1123.*

* cited by examiner

*Primary Examiner* — Vera Afremova
(74) *Attorney, Agent, or Firm* — The Webb Law Firm

(57) ABSTRACT

This invention relates to a process for the production of organic formulation of bio pesticide containing *Pseudomonas Fluorescens* comprising preparation of Mother culture of *P. fluorescens* and inoculating in King's B broth, at 30±1° C. for 24-36 hours followed by liquid fermentation process in 5-10% pongamia cake aqueous extract, 5-10% neem cake aqueous extract, 0.3-0.5% sugarcane molasses and King's B broth followed by solid fermentation using sterile Pongamia deoiled cake, Neem deoiled cake, wheat Bran.

4 Claims, No Drawings

PROCESS FOR THE PRODUCTION OF ORGANIC FORMULATION OF BIO-PESTICIDE PSEUDOMONAS FLUORESCENS

FIELD OF THE INVENTION

This invention relates to a process for the production of organic Formulation of Bio-Pesticide containing *Pseudomonas Fluorescens*.

BACKGROUND OF INVENTION

Earlier researchers had standardized a process of mass production of *Pseudomonas Fluorescens* using Kings B broth and carrier is talc powder. This process included only liquid fermentation step and not solid fermentation. As it is liquid fermentation process alone would result in the end product of bio-control agent formulation of inferior quality. Hence by this process it will not be economical to produce the formulation of bio control agent *P. fluorescens*.

For the management of various soil borne pathogens, formulation of *P. fluorescens* is being used widely on the various agricultural crops in the world. There are also several reports on the production methods of *P. fluorescens* using various carrier materials such as talc and vermiculite. Various researchers reported on the various types of formulations using different carriers. However there is no information on the use of pongamia cake, neem cake and wheat bran for the solid fermentation of this bioagent, till today in the world.

OBJECTS OF THE INVENTION

Object of this invention is to develop a process for the production of organic formulation of biopesticide *Pseudomonas Fluorescens*.

Other object is to develop an organic formulation with an organic carrier.

Another object is to use the novel technique of solid fermentation of *P. fluorescens* after the liquid fermentation.

Yet another object is to use organic carrier for the formulation after the solid fermentation of *Pseudomonas Fluorescens*.

DETAILED DESCRIPTION OF THE INVENTION

The process for the production of organic formulation of bio pesticide containing *Pseudomonas Fluorescens* consists of:

1. Preparation of mother culture of *P. fluorescens* by taking out discs and inoculating in King's B broth, incubating at specific temperature of 30±1° C. for specific time 24-36 hours.
2. Liquid fermentation process is done in 5-10% pongamia cake aqueous extract, 5-10% neem cake aqueous extract prepared by pre soaking the oil cake 5-10 kg in 100 liters tap water and later decant and filter through muslin cloth, 0.3-0.5% sugarcane molasses prepared by dissolving 300-500 ml molasses in 100 liters tap water and sterilized and King's B broth in the ratio of 1:1:1:1.
3. Solid fermentation is done using sterile Pongamia deoiled cake, Neem deoiled cake, wheat Bran in the ration of 3:4:3.

The *Pseudomonas Fluorescens* obtained through liquid fermentation is mixed at the rate of 25 ml per kg of solid fermentation substrate filled in a tray with lid and left for 10 days for solid fermentation.

Characteristics of Formulation

Neem and pongamia cakes were used as the carrier of the formulation of the product. This is also unique since this improves the establishment of the bio-control agent in the soil, it will be economical, eco-friendly and fits in organic farming practices.

Spore load (spores of bio-agent): $5.5 \times 10^9$ cfu/gram of product

Moisture percentage—8%

Shelf life of the product—12 months

The bio efficacy of the formulation was generated against, *Rolstania solanecearum, Erwinia caratovora, Fusarium oxysporum, Rotylenchulus reniformis, Tylenchulus semi penetrans, Meloidogyne incognita* infecting horticultural crops such as tomato, egg plant, capsicum, acid lime, banana, papaya, guava, carnations, crossandra and tuberose. The efficacy of the formulation was also tested in the production of bio-agent colonized seedlings of tomato, egg plant, capsicum, acidlime, banana, papaya, guava, carnations, crossandra.

Quality:

Colony Forming Units (CFU) of *P. fluorescens* on selective medium is $5.5 \times 10^9$/g Pathogenic contaminants Salmonella—not present Shigella—not present Vibrio—not present.

Other microbial contaminants are $1.6 \times 10^2$ count/gm

Maximum moisture content is 9.0% pH is 7.1

In this invention, because of the presence of neem and pongamia the efficacy of this bioagent against various soil borne pathogens infecting various agricultural crop is very high. Solid fermentation is an important step and contributes tremendously for the mass production process making it more efficient and economical.

Example

Preparation of Mother Culture of *P. Fluorescens*

The isolate has to be sub cultured on King's B– agar medium. It should be incubated for 24-36 hours 30±1° C. Later with the help of cork borer (7 mm) the discs should be cut and inoculate into the 500 ml conical flask containing 250 ml of King's B broth. This has to be incubated at 30±1° C. for 24-36 hours and this can be used for the liquid fermentation.

Liquid Fermentation Process:

Organic materials (5-10%—pongamia cake aqueous extract+5-10%-neem cake aqueous extract+0.3-0.5% sugar cane molasses+King' B broth in the ratio of 1:1:1:1) are used as substrate for the liquid fermentation.

The required concentration of 5-10% of neem and pongamia aqueous extracts have to be prepared by pre-soaking the oil cake 5-10 kg overnight in 100 liters of tap water and later decant and filter through muslin cloth.

The required concentration of 0.3-0.5% of Molasses (organic material) has to be prepared by dissolving 300-500 ml molasses of 100 liters tap water. All the ingredients have to be mixed, autoclaved. 121° C. (15 PSI) for 20 min. and should be used as the substrate in the liquid fermentation process.

Solid Fermentation of *P. Fluorescens*:

*Pseudomonas Fluorescens* obtained through the liquid fermentation has to be used for solid fermentation using organic materials.

The composition of the substrate (organic materials) to be used in the solid fermentation is Pongamia (de oiled) cake: Neem (de oiled) cake: Wheat Bran in ration of 3:4:3.

These materials have to be autoclaved at 121° C. (15 PSI) for 20 min.

Inoculation of *P. Fluorescens* on to Organic Materials in the Solid Fermentation:

*Pseudomonas Fluorescens* obtained through the liquid fermentation has to be mixed rate of 25 ml per kg of the above substrate filled in a tray with the lid and should be left or 10 days for the solid fermentation.

Production of the Organic Formulation (Final Product) of the Bio-Agent *P. Fluorescens:*

The material obtained through the solid fermentation of *P. fluorescens* can be packed one or five or ten kg packets in aseptic conditions. Hence the organic materials (Neem (de oiled) cake+Pongamia (de oiled) cake Wheat Bran) will become carrier material of the formulation or product of this bio-agent.

Protocol for production of organic formulation of *Pseudomonas Fluorescens*

Liquid fermentation of *P. fluorescens* using 5% pongamia cake aqueous extract + 5% neem cake aqueous extract + 0.03% sugar cane molasses + King' B medium in the ratio of 1:1:1:1

↓

Solid fermentation of *P. fluorescens* using Pongamia (de oiled) cake: Neem (de oiled) cake:Wheat Bran in the ratio of 3:4:3

↓

Production of the organic formulation (final product) of *P. fluorescens* and packing the bio-pesticide

↓

Packaging into 1 or 5 kg units

It is to be noted that the formulation of the present invention is susceptible to modifications, adaptations and changes by those skilled in the art. Such variant formulations are intended to be within the scope of the present invention which is further set forth under the following claims:

I claim:

1. A process for the production of organic formulation of biopesticide containing *Pseudomonas fluorescens* comprising:

a first step of preparing a Mother culture of *P. fluorescens* and inoculating in King's B broth, at 30±1° C. for 24-36 hours;

a second step of liquid fermentation of the culture obtained through inoculating the Mother culture in King's B broth in a first substrate comprising 5-10% pongamia cake aqueous extract, 5-10% neem cake aqueous extract, 0.3-0.5% sugarcane molasses and King's B broth;

followed by a third step of solid fermentation of the culture obtained through liquid fermentation in a second substrate comprising sterile Pongamia deoiled cake, Neem deoiled cake, and Wheat Bran.

2. The process as claimed in claim 1 wherein the required concentration of neem and pongamia aqueous extracts are prepared by presoaking the oilcake 5-10 kg in 100 liters tap water and later decant and filter through muslin cloth.

3. The process as claimed in claim 1 wherein the required concentration of Molasses is prepared by dissolving 300-500 ml molasses in 100 liters tap water and sterilized.

4. The process as claimed in-claim 1, wherein the culture obtained through liquid fermentation is mixed at the rate of 25 ml per kg of solid fermentation substrate filled in a tray with lid and left for 10 days for solid fermentation.

* * * * *